United States Patent
Raddatz

(10) Patent No.: US 7,072,029 B2
(45) Date of Patent: Jul. 4, 2006

(54) METHOD AND APPARATUS FOR TESTING OPTICAL FIBER CABLES

(75) Inventor: Lutz Raddatz, Nuremberg (DE)

(73) Assignee: Lucent Technologies Inc., Murray Hill, NJ (US)

( * ) Notice: Subject to any disclaimer, the term of this patent is extended or adjusted under 35 U.S.C. 154(b) by 33 days.

(21) Appl. No.: 10/851,582

(22) Filed: May 21, 2004

(65) Prior Publication Data

US 2005/0259243 A1 Nov. 24, 2005

(51) Int. Cl.
*G01N 21/00* (2006.01)

(52) U.S. Cl. .................................... 356/73.1

(58) Field of Classification Search ..................... None
See application file for complete search history.

(56) References Cited

U.S. PATENT DOCUMENTS

| | | | | |
|---|---|---|---|---|
| 5,757,311 A | * | 5/1998 | Voyce | 342/130 |
| 6,081,127 A | * | 6/2000 | Wagner et al. | 324/765 |
| 6,316,943 B1 | * | 11/2001 | Yamashita et al. | 324/606 |

* cited by examiner

*Primary Examiner*—Tu T. Nguyen
(74) *Attorney, Agent, or Firm*—Matthew J. Hodulik; Gregory J. Murgia

(57) ABSTRACT

An optical fiber cable is tested to determine the zero dispersion frequencies of the sections of which it is made by directing light along it, the light comprising two optical frequency components having optical frequencies that differ by a predetermined amount $\Delta\omega$. The frequencies of the components are swept across the operating frequency range of the cable, keeping $\Delta\omega$ constant. At the other end of the cable, the spectrum of the light is analyzed to determine the relative powers of first order 4 WM components (satellite lines) and the frequencies at which they have principal maximum values.

17 Claims, 2 Drawing Sheets

METHOD AND APPARATUS FOR TESTING OPTICAL FIBER CABLES

TECHNICAL FIELD

This invention relates to methods and apparatus for testing optical fiber cables.

BACKGROUND OF THE INVENTION

Optical fibers have proven to be capable of carrying large amounts of data over long distances. However, there is always a demand for more data-carrying capacity, since each increase in capacity is soon followed by new applications that use it. One of the limitations on the data-carrying capacity of an optical fiber is chromatic dispersion. Since an optical pulse inherently contains a range of optical frequencies, if the velocity of an optical signal through a fiber depends on its frequency, the pulse will become broader as it propagates through the fiber, eventually reaching a point at which one pulse starts to interfere with neighboring pulses.

Standard single mode optical fiber has a zero dispersion wavelength, i.e. a wavelength at which the velocity of the signal as a function of frequency has a stationary value, in the range 1300 to 1324 nm. Therefore, the effects of chromatic dispersion are kept to a minimum as long as the fiber is used at a wavelength in this range.

For a number of reasons, however, the 1300 nm wavelength band is not the preferred wavelength band in which to operate. The loss minimum for the silica-based fibers that are currently prevalent falls at a wavelength of about 1550 nm and the erbium-doped fiber amplifier also works at around this wavelength, so the preferred wavelength band is now the 1550 nm band, which extends from about 1535 nm to about 1565 nm. New erbium-doped fiber amplifiers can use the wavelength range of 1530 nm to 1610 nm.

Therefore, a considerable effort has been put into designing optical fibers in which the refractive index profile, combined with the dispersion characteristics of the material, combine to produce a zero dispersion wavelength in the 1550 nm band, preferably at approximately 1550 nm. This is known as "dispersion shifted fiber" (DSF). A considerable amount of DSF has been made and installed and is in use.

In a further effort to increase data carrying capacity, attention has turned to wavelength division multiplexing (WDM) which is a way of increasing capacity by using a number of different wavelengths within the wavelength band of choice, each wavelength providing a channel which carries data signals independently of the channels at other wavelengths. Thus, the data carrying capacity of a fiber can be multiplied several times. Naturally, it is required to have as many different wavelengths carrying data as possible, so it is preferred to employ many closely spaced wavelengths to maximize the capacity. This is known as dense wavelength division multiplexing (DWDM).

A problem arises, however, when WDM, and especially DWDM, is used in dispersion shifted fiber, owing to a phenomenon known as "four wave mixing" (4 WM) or sometimes "four photon mixing". This is a non-linear effect, which arises when the optical intensity in the fiber is high, as it has to be, at least when the optical signal is introduced into the fiber, in order to achieve a satisfactory transmission distance. When there are optical signals at two closely spaced frequencies, $\omega_1$ and $\omega_2$, 4 WM produces signals having frequencies of $2\omega_1-\omega_2$ and $2\omega_2-\omega_1$, or, assuming that $\omega_2>\omega_1$, and setting $\Delta\omega=\omega_2-\omega_1$, it produces signal having frequencies of $\omega_2+\Delta\omega$ and $\omega_1-\Delta\omega$. This provides a loss mechanism, reducing the power of the original signals at frequencies $\omega_1$ and $\omega_2$, but also, and more damagingly, it produces cross-talk between different frequencies, since if the frequencies are equally spaced, which they will be, to fit the maximum number of channels into the wavelength band, the signals produced from two channels by 4 WM will coincide in frequency with adjacent channels at frequencies above and below those of the original two. 4 WM also causes problems with high bit rate (e.g. 40 Gb/s) systems using high transmission power.

Normally, the magnitude of 4 WM is limited, and it is quite a small effect. This is because of chromatic dispersion, which causes the different signal wavelengths to have different velocities, thereby reducing its efficiency. However, if the dispersion is zero or close to zero, 4 WM effects can build up and become a very serious limitation on the use of WDM.

As well as 4 WM, there is another non-linear effect that degrades the performance of DWDM systems at wavelengths near the zero dispersion wavelength. This effect is known as Cross-Phase Modulation (XPM). Here the rising and falling edges of one signal slightly change the refractive index of the fiber, thereby distorting the other signals of DWDM system. This effect is again most efficient when different wavelengths move along the fiber at the same speed (as is the case at or near the zero dispersion wavelength), as the interaction between the signals is maximized.

In fact, the preferred fiber for use with DWDM is so-called "non-zero dispersion shifted fiber" which has a small, but non-zero, dispersion throughout the wavelength band, typically in the range 1.5–4 ps/nm-km (see, for example U.S. Pat. No. 5,587,830).

However, there is a large legacy of DSF installed, and it is possible to increase its data carrying capacity by using WDM, or by using high bit rates at high power, as long as the wavelengths used keep clear of the zero dispersion wavelength. To keep clear of the zero dispersion wavelength, of course, it is necessary to know what its value is.

It would be possible to actually measure the dispersion of a cable, end-to-end, for a number of different wavelengths in the band, and to find the zero dispersion wavelength in that way, but there is a problem with this approach. In the manufacture of DSF, fiber sections of several km in length from different production runs are spliced together to form one long cable. This has the advantage, from the point of view of DSF, that the overall dispersion of the cable is an average of the dispersions of the various sections, so variations in the zero dispersion wavelength between different production runs are averaged out and the final cable has a zero dispersion wavelength which is more closer to the design value than would be possible in any one production run. Therefore, the zero dispersion wavelength of the cable as a whole does not necessarily correspond to the zero dispersion wavelength of any particular section of it.

To be able to use WDM in a DSF cable, or generally to avoid 4 WM, the wavelengths to avoid are the zero dispersion wavelengths of the sections of the cable nearest to the end of the cable at which the signals are inserted, because those are the sections in which the optical intensity is highest and in which 4 WM is therefore most severe. When the signals have propagated through several sections of the cable, they have become attenuated, and 4 WM, which is a high order non-linear effect, ceases to be a great problem.

SUMMARY OF THE INVENTION

According to the principles of the invention, a method and apparatus are provided for determining zero dispersion wavelengths of optical fibers in optical fiber cables. In one illustrative embodiment, a method of testing an optical fiber cable comprises directing light along the cable from a first end to a second end thereof, the light including two optical frequency components having optical frequencies that differ by a predetermined amount $\Delta\omega$, sweeping the frequencies of the components of the light across the operating frequency range of the cable, keeping the predetermined amount $\Delta\omega$ substantially constant and, during the sweeping, analyzing the spectrum of the light as it emerges from the second end of the cable to determine the relative powers of first order 4 WM components (satellite lines) and the frequencies at which the relative powers have principal maximum values.

In another illustrative embodiment, a method carried out at a first end of an optical fiber cable comprises directing light along the cable from the first end to a second end thereof, the light including two optical frequency components having optical frequencies that differ by a predetermined amount $\Delta\omega$ and sweeping the frequencies of the components of the light across the operating frequency range of the cable, keeping the predetermined amount $\Delta\omega$ substantially constant.

According to another illustrative embodiment, a method carried out at a second end of an optical fiber cable comprises receiving light directed along the cable from a first end to the second end thereof, the light including two optical frequency components having optical frequencies that differ by a predetermined amount $\Delta\omega$, the frequencies of the components of the light being swept across the operating frequency range of the cable, keeping the predetermined amount $\Delta\omega$ substantially constant and, during the sweeping, analyzing the spectrum of the light as it emerges from the second end of the cable to determine the relative powers of first order 4 WM components (satellite lines) and the frequencies at which the relative powers have principal maximum values.

According to another illustrative embodiment, apparatus for testing an optical fiber cable comprises a light source for directing light along the cable from a first end to a second end thereof, the light including two optical frequency components having optical frequencies that differ by a predetermined amount $\Delta\omega$ and control means coupled to the light source for sweeping the frequencies of the components of the light across the operating frequency range of the cable, keeping the predetermined amount $\Delta\omega$ substantially constant.

DETAILED DESCRIPTION

Figure 1:
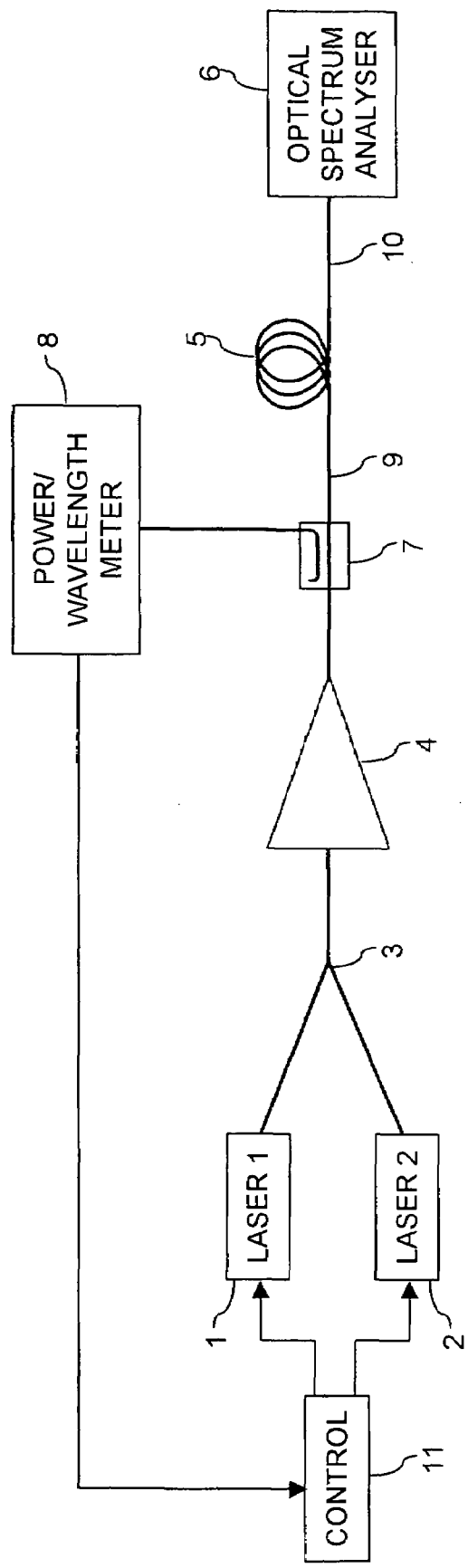
FIG. 1 shows apparatus set up to test an optical fiber cable by a method according to the present invention.

FIG. 1 shows a first laser 1 and a second laser 2 with their optical outputs connected to an optical combiner 3, typically with a 3 dB coupling ratio. The output of the optical combiner 3 is connected via an optical amplifier 4 to the optical cable 5 that is under test. The optical amplifier may not be required if lasers with sufficiently high output power are available. The remote end of the optical cable 5 is connected to an optical spectrum analyzer 6. Between the optical amplifier 4 and the cable 5, a 10 dB tap coupler 7 is connected to tap off a portion of the optical signal, which is connected to a wavelength meter or optical spectrum analyzer 8 for monitoring purposes.

Figure 2:
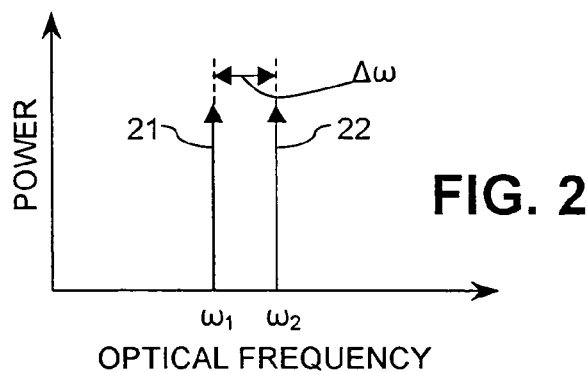
FIG. 2 shows the spectrum of a signal to be transmitted into an optical fiber cable in a method according to the present invention.

In use, the lasers 1 and 2 are set up to provide light of slightly different frequencies, typically differing by about 50 GHz (equivalent, for light in the 1550 nm band, to a wavelength difference of about 0.4 nm). The spectrum of the combined optical signal is shown in FIG. 2, in which the lines 21 and 22, produced by the respective lasers, 1 and 2, are at frequencies $\omega_1$ and $\omega_2$, the frequency difference being shown as $\Delta\omega$. The frequencies, $\omega_1$ and $\omega_2$, are swept across the frequency band, keeping the frequency difference $\Delta\omega$ constant. Tunable lasers with an accuracy of <2 GHz (0.016 nm) are available, which is sufficient for the present purpose. Furthermore, the power/wavelength meter 8 can measure wavelengths to 0.008 nm (1 GHz) accuracy, and can be used to control the lasers 1 and 2 by providing feedback to a control circuit 11 to achieve even greater precision, as well as controlling the output power of the lasers 1 and 2 to maintain them equal to one another and at a desired level, which is typically of the order of the power intended to be used in transmission over the cable 5.

Figure 3:
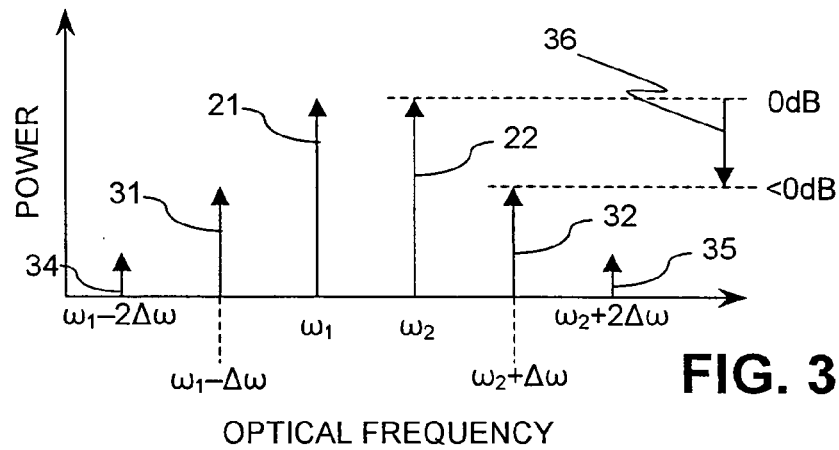
FIG. 3 shows the spectrum of a signal as received from an optical fiber cable in a method according to the present invention and FIG. 4 shows a plot of measurements taken during a method according to the present invention, from which zero-dispersion wavelengths may be determined.

FIG. 3 shows the power spectrum of the optical signal received and measured by the optical spectrum analyzer 6 at a particular instant. In addition to the principal lines 21 and 22, at the frequencies $\omega_1$, and $\omega_2$ emitted by the lasers, 1 and 2, there are satellite lines 31 and 32, at frequencies $\omega_1-\Delta\omega$ and $\omega_2+2\Delta\omega$, generated by 4 WM and second order lines 33 and 34, at frequencies $\omega_1-2\Delta\omega$ and $\omega_2+2\Delta\omega$, generated by higher-order 4 WM. The relative power of the 4 WM-generated satellite lines, 31 and 32, relative to the principal lines 21 and 22, is monitored as the frequencies emitted by the lasers 1 and 2 are swept across the frequency band. This relative power is shown as 35 in FIG. 3, and is the difference in height between the lines, which are plotted on a logarithmic (dB) scale.

Figure 4:
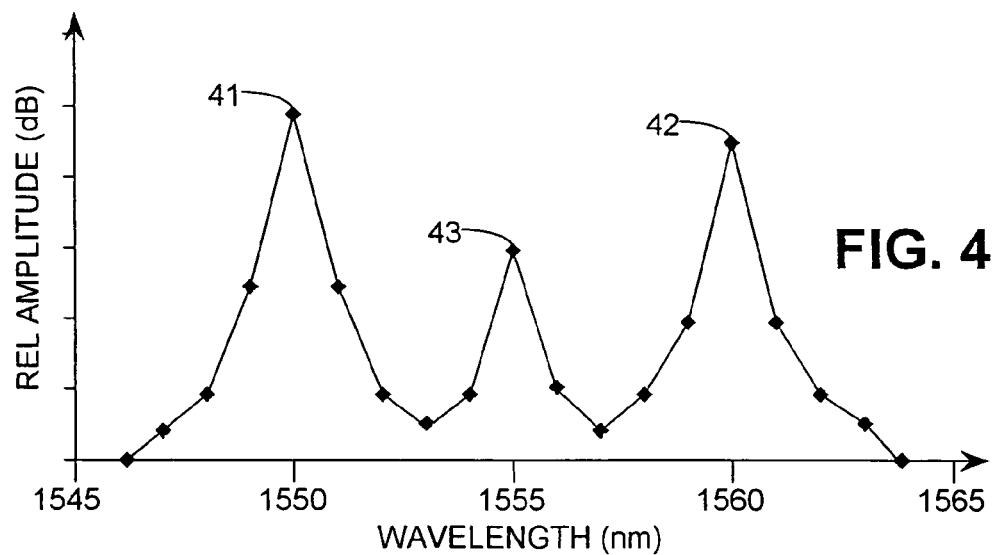

FIG. 4 shows a typical plot of relative power versus signal wavelength. Hitherto in the discussion, we have referred to the frequency to characterize the optical signal, since for theoretical purposes the frequency f, and the angular frequency $\omega=2\pi f$, being closely related to the photon energy, are particularly pertinent. However, for practical purposes it is more convenient to refer to the vacuum wavelength $\lambda$, hence the change of terminology between FIG. 3 and FIG. 4. The frequency f is related to the vacuum wavelength $\lambda$ by the well-known relation $\lambda f=c$, where c is the speed of light in vacuo. By "signal wavelength" is meant the wavelength corresponding to the average frequency of the two optical signals, i.e. $(\omega 1+\omega 2)/2$ or, which is for practical purposes the same, the average of the wavelengths corresponding to $\omega 1$ and $\omega 2$ respectively.

FIG. 4 shows three maxima, 41, 42 and 43, in the relative power of the satellite lines. These occur at the zero dispersion points of the fiber sections nearest to the first end 9 of the cable 5 to which the lasers 1 and 2 are connected, and at which the power of the optical signal is greatest. In this particular case, there is, in order of decreasing magnitude, a main maximum 41 at 1550 nm, indicating that that is the zero dispersion wavelength for the first section of fiber, a second maximum 42 at 1560 nm, indicating that that is the zero dispersion wavelength for the second section, and a third maximum 43 at 1555 nm, indicating that that is the zero dispersion wavelength for the third section. No other maxima are visible, which indicates that 4 WM is negligible in subsequent sections of the cable.

Advantageously, according to the principles of the invention, the zero dispersion wavelengths can be determined for the sections of cable that are nearest to the end of the cable at which the optical signals are to be inserted because those are the sections in which the optical intensity is highest and in which 4 WM is therefore most severe. For communications in the direction from the first end 9 of the cable 5 to the opposite end 10, therefore, the wavelengths to avoid are the wavelengths corresponding to the maxima 41, 42 and 43. For communications in the opposite direction it is desirable to perform the test again in the opposite direction, i.e., with the lasers 1 and 2, optical combiner 3, optical amplifier 4, tap coupler 7 and wavelength meter 8 connected to the opposite end 10 of the cable 5 and the optical spectrum analyzer 6 connected to the first end 9. This is because the important sections of the cable are then those nearest to the opposite end 10 of the cable, and these may have different zero dispersion wavelengths from those sections nearest to the first end 9.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method of testing an optical fiber cable, comprising:
   directing light along said cable from a first end to a second end thereof, said light including two optical frequency components having optical frequencies that differ by a predetermined amount $\Delta\omega$;
   sweeping the frequencies of the components of said light across the operating frequency range of said cable, keeping said predetermined amount $\Delta\omega$ substantially constant; and
   during said sweeping, analyzing the spectrum of said light as it emerges from said second end of the cable to determine the relative powers of first order four wave mixing (4 WM) satellite lines and the frequencies at which said relative powers have principal maximum values.

2. The method of claim 1, further comprising:
   directing further light along said cable from said second end to said first end, said further light including two optical frequency components having optical frequencies that differ by said predetermined amount;
   sweeping the frequencies of the components of said further light across the operating frequency range of said cable, keeping said predetermined amount substantially constant; and
   during said sweeping, analyzing the spectrum of said further light as it emerges from said first end of the cable to determine the relative powers of first order 4 WM satellite lines and the frequencies at which said relative powers have principal maximum values.

3. The method of claim 1, wherein said predetermined amount is less than about 100 GHz.

4. The method of claim 3, wherein said predetermined amount is about 50 GHz.

5. The method of claim 1, wherein said predetermined amount is kept constant to within 4 GHz.

6. The method of claim 5, wherein said predetermined amount is kept constant to within 2 GHz.

7. A method carried out at a first end of an optical fiber cable comprising:
   directing light along said cable from said first end to a second end thereof said light including two optical frequency components having optical frequencies that differ by a predetermined amount $\Delta\omega$; and
   sweeping the frequencies of the components of said light across the operating frequency range of said cable, keeping said predetermined amount $\Delta\omega$ substantially constant.

8. The method of claim 7, wherein said predetermined amount is less than about 100 GHz.

9. The method of claim 8, wherein said predetermined amount is about 50 GHz.

10. The method of claim 7, wherein said predetermined amount is kept constant to within 4 GHz.

11. The method of claim 10, wherein said predetermined amount is kept constant to within 2 GHz.

12. A method carried out at a second end of an optical fiber cable comprising:
    receiving light directed along said cable from a first end to said second end thereof said light including two optical frequency components having optical frequencies that differ by a predetermined amount $\Delta\omega$, the frequencies of the components of said light being swept across the operating frequency range of said cable, keeping said predetermined amount $\Delta\omega$ substantially constant; and
    during said sweeping, analyzing the spectrum of said light as it emerges from said second end of the cable to determine the relative powers of first order four wave mixing (4 WM) satellite lines and the frequencies at which said relative powers have principal maximum values.

13. Apparatus for testing an optical fiber cable comprising:
    a light source for directing light along said cable from a first end to a second end thereof, said light consisting essentially of two optical frequency components having optical frequencies that differ by a predetermined amount $\Delta\omega$; and
    control means coupled to said light source for sweeping the frequencies of the components of said light across the operating frequency range of said cable, keeping said predetermined amount $\Delta\omega$ substantially constant.

14. The apparatus of claim 13, wherein said predetermined amount is less than about 100 GHz.

15. The apparatus of claim 14, wherein said predetermined amount is about 50 GHz.

16. The apparatus of claim 13, wherein said predetermined amount is kept constant to within 4 GHz.

17. The apparatus of claim 16, wherein said predetermined amount is kept constant to within 2 GHz.

* * * * *